US00PP08233P

United States Patent [19]

Jessel, Jr.

[11] Patent Number: Plant 8,233

[45] Date of Patent: May 18, 1993

[54] CARNATION PLANT NAMED CFPC GRENADA

[75] Inventor: Walter H. Jessel, Jr., Salinas, Calif.

[73] Assignee: California Florida Plant Co., L.P., Salinas, Calif.

[21] Appl. No.: 757,907

[22] Filed: Sep. 11, 1991

[51] Int. Cl.[5] ..... A01H 5/00

[52] U.S. Cl. ..... Plt./70.7

[58] Field of Search ..... Plt./70.1, 70.7

[56] References Cited

U.S. PATENT DOCUMENTS

P.P. 5,439 4/1985 Barberet et al. ..... Plt. 70.7

*Primary Examiner*—Howard J. Locker

*Attorney, Agent, or Firm*—Christie, Parker & Hale

[57] ABSTRACT

A new carnation of red coloration.

1 Drawing Sheet

SUMMARY OF THE INVENTION

The present invention relates to a new and distinct variety of carnation plant which was originated by me in a controlled breeding program by my crossing as seed and pollen parents, the variety known as 'Etna' (varietal denomination 'Lonsoury') and as pollen parent, the variety known as 'Rony' (varietal denomination 'Aroni'). The varietal denomination of this new carnation is 'CFPC Grenada'.

Among the novel combination of characteristics possessed by the new variety which distinguishes 'CFPC Grenada' are attractive red flower coloring, superior resistance to soil born diseases such as *Fusarium oxysporium* and *F. roseum* and root-rot, and satisfactory flowering response. Flowers of the new variety are produced as spray-type blooms which open fully without bursting the calyx and causing "splits", on a very vigorous plant with strong, straight sprays.

'CFPC Grenada' differs from its seed parent 'Lonsoury' in having a less serrated petal edge, a darker red, less scarlet flower coloration and in being 4 to 5 weeks faster to flower from the same planting date. The new variety is also 5 to 6-inches shorter and averages 2 to 3 more breaks per plant after pinching.

Asexual reproduction by propagation by side shoot cuttings of the new variety as performed in Fremont and Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Grenada'.

BRIEF DESCRIPTION OF THE ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering depending upon varying environmental, seasonal and cultural conditions.

The information provided herein is based on observations of plants grown inside commercial greenhouses at Fremont and Salinas, Calif. The height of plant and flower and foliage size are established as an average using standard commercial cultural practices.

Name: 'CFPC Grenada'.

Classification:

*Botanical.*—*Dianthus caryophyllus.*

*Commercial.*—Carnation, spray type.

Parentage:

*Female parent.*—'Etna'.

*Male parent.*—'Rony'.

Plant:

*Height.*—About 36 inches.

*Growing habit.*—Herbaceous, semi-upright.

*Blooming habit.*—Terminal as a spray.

*Blooming season.*—Year round.

*Rooting time.*—About 16–17 days.

*Mutation prone.*—Does not appear to be.

*Disease resistance.*—Improved resistance to Fusarium species and water molds.

*Temperature tolerance.*—Wide range for carnation.

*Breaking action.*—Average.

Foliage:

*Color.*—Upper side: Near to 143A. Lower side: Near to 143C.

*Size.*—About 5-inches long, about ½-inch wide, at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About ¾ inch.

*Diameter.*—About ½ inch.

Calyx:

*Number of lobes (sepals).*—Usually 6.

*Length.*—About 1-inch.

*Width.*—About ½-inch.

*Color.*—Outside — near to 143A. Inside — near to 142D.

Bloom:

*Shape.*—Round.

*Size.*—Diameter average: About 2½ inches. Depth average: About 1½ inches.

*Borne.*—Terminal as a spray.

*Color.*—General tonality: Dark red. Upper side: Near to from 45A to 46B. Lower side: Near to 45C. Center: Near to from 45A to 46B. Outer petals: Near to from 45A to 46B.

*Keeping quality.*—Good.

*Fragrance.*—None to slight.

*Permanence.*—Dry up on receptacle.

Petals:

*Number.*—About 39.

*Outer petals.*—Length: About 2-inches. Width: About 1-inch.

*Central petals.*—Length: About 1-inch. Width: About ½-inch.

*Texture.*—Smooth.

*Form.*—Fan shaped.

*Appearance.*—Shiny smooth edge.

Reproductive organs: Not visible in this variety.

*Stamens.*—Number: About 9 to 12. Arrangement: Around the ovary.

*Anthers.*—Length: About ⅜-inch. Color: Near to 160C.

*Filaments.*—Length: About ⅔-inch. Color: Near to 161B.

*Pistil.*—Number: About 2 to 3. Color: White.

*Stigma.*—Number: About 2 to 3. Color: White.

*Ovary.*—Shape: Conical, ribbed. Color: Base — greenish white. Body — greenish yellow. Apex — tan.

I claim:

1. A new and distinct variety of carnation plant, substantially as shown and described.

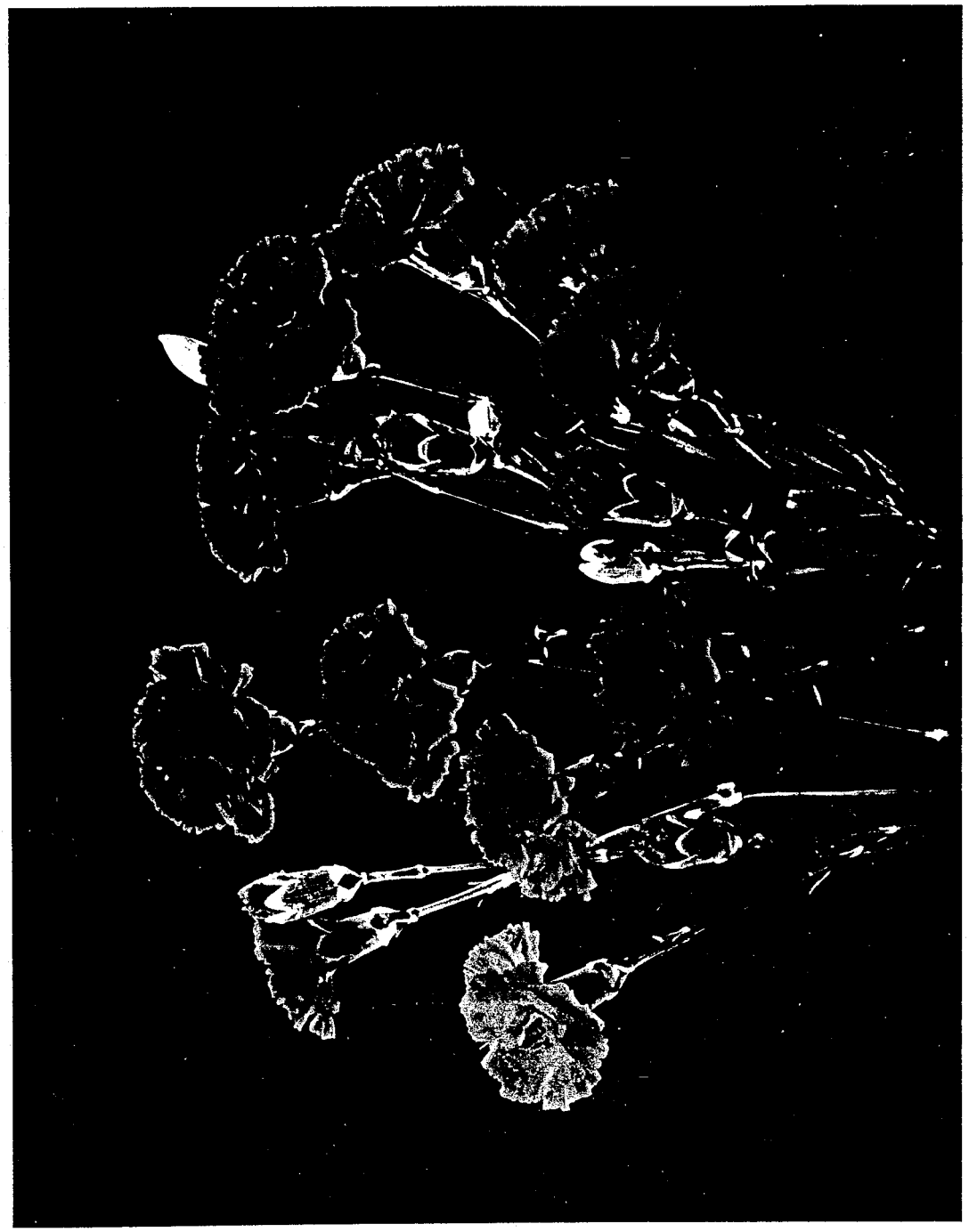

* * * * *